United States Patent [19]

Dudman

[11] Patent Number: 5,430,203
[45] Date of Patent: Jul. 4, 1995

[54] PROCESS FOR THE REDUCTION OF HALOCARBONS

[75] Inventor: Christopher C. Dudman, Lache Park, England

[73] Assignee: Imperial Chemical Industries PLC, London, United Kingdom

[21] Appl. No.: 195,058

[22] Filed: Feb. 14, 1994

Related U.S. Application Data

[63] Continuation of Ser. No. 917,294, Jul. 23, 1992, abandoned.

[30] Foreign Application Priority Data

Jul. 26, 1991 [GB] United Kingdom ............... 9116206

[51] Int. Cl.$^6$ ............................................. C07C 19/08
[52] U.S. Cl. .................................................. 570/176
[58] Field of Search ......................................... 570/176

[56] References Cited

FOREIGN PATENT DOCUMENTS

| | | | |
|---|---|---|---|
| 490147 | 6/1992 | European Pat. Off. | 570/176 |
| 3130238 | 6/1991 | Japan | 570/176 |
| 3130239 | 6/1991 | Japan | 570/176 |
| 939920 | 10/1963 | United Kingdom | 570/176 |

*Primary Examiner*—Alan Siegel
*Attorney, Agent, or Firm*—Cushman, Darby & Cushman

[57] ABSTRACT

A process for the reduction of a halocarbon containing a group having the formula —$CX_2Y$ wherein X is Cl, Br, or I and Y is Cl, Br, I or F; in particular 1,1,1-trichloro-2,2,3,3,3-pentafluoroethane, by subjecting the halocarbon to a reduction reaction in an aqueous solution of an alkali metal sulphite or ammonium sulphite as reducing agent and an acid acceptor, in which the acid acceptor is also an alkali metal sulphite or ammonium sulphite.

13 Claims, No Drawings

PROCESS FOR THE REDUCTION OF HALOCARBONS

This is a continuation of application Ser. No. 07/917,294, filed on Jul. 23, 1992, now abandoned.

This invention relates to a process for the reduction of halocarbons and more particularly to a process for the reduction of halocarbons containing a —$CX_2Y$ group in which X is Cl, Br, or I, and Y is Cl, Br, I or F to produce halocarbons containing the group —CHXY. The process is one in which an alkali metal sulphite or ammonium sulphite is used as reducing agent.

Processes are known for the reduction of halocarbons in which sodium sulphite is used as the reducing agent. Thus, in GB Patent Publication No. 2 210 880 there is described a process for the production of 1,1-dichloro-2,2,2-trifluoroethane from trichlorotrifluoroethane by reduction of trichlorotrifluoroethane in an aqueous solution of sodium sulphite and an acid acceptor such as an alkali metal or alkaline earth metal hydroxide, carbonate or acetate.

However, the process of GB 2 210 880 suffers from the disadvantage that there is a competing elimination reaction of which the product is the highly toxic alkene difluorodichloroethene, $CF_2=CCl_2$. We have found that application of the process of GB 2 210 880 to other two carbon and three carbon starting halocarbons also tends to result in the formation of alkene by-products. The production of such alkenes is particularly undesirable because they are in general extremely toxic materials which must be removed completely from any commercial product or at least reduced to very low levels, for example to below 5 ppm.

The separation of such alkene by-products is difficult and expensive, and furthermore processes for their removal have the effect of reducing the amount of the desired product which is produced.

The present invention resides in a process for the reduction of halocarbons using an alkali metal sulphite or ammonium sulphite as the reducing agent in which the amount of toxic alkene produced may be substantially reduced.

The production of unwanted alkene by-products in sodium sulphite reduction reactions is promoted, at least to some extent, by the use of a strong base, for example sodium hydroxide, as the acid acceptor. Thus in GB 2 210 880 fifteen times as much alkene is produced when the strong base sodium hydroxide is used as the acid acceptor than when the weak base sodium acetate is used as the acid acceptor.

We have now found that the use of an alkali metal sulphite or ammonium sulphite as the acid acceptor, despite their being stronger bases than sodium acetate, leads to a substantial reduction in the amount of alkene formed even when compared to the amount of alkene formed when sodium acetate is used.

According to the present invention there is provided a process for the reduction of a halocarbon containing a group having the formula $CX_2Y$ wherein X is Cl, Br, or I and Y is Cl, Br, I or F which process comprises subjecting the halocarbon to a reduction reaction in an aqueous solution of an alkali metal sulphite or ammonium sulphite and an acid acceptor, characterised in that the acid acceptor is an alkali metal sulphite or ammonium sulphite. Thus, sufficient (as hereinafter described) of one or more alkali metal sulphites or ammonium sulphite are provided in order that they may act as both reducing agent and acid acceptor during the reaction.

In the process of the invention one chlorine, bromine or iodine atom of the halocarbon to be reduced is substituted by a hydrogen atom. This substitution reaction is accompanied by the formation of hydrogen chloride but this acidic by-product is readily neutralised by the acid acceptor contained in the aqueous solution.

The alkali metal sulphite may be, for example, potassium or sodium sulphite. Preferably the reducing agent employed is sodium sulphite.

The use of an alkali metal sulphite or ammonium sulphite as the acid acceptor in the process of the invention leads to a substantial reduction in the amount of any alkene produced by the competing elimination reaction in the process. The alkali metal sulphite used as acid acceptor may be, for example, potassium or sodium sulphite; preferably it is sodium sulphite.

In a preferred embodiment of the invention, the same alkali metal sulphite or ammonium sulphite, especially sodium sulphite, is used as both the reducing agent and the acid acceptor, that is sufficient (as hereinafter described) of a single alkali metal sulphite or ammonium sulphite, preferably sodium sulphite, is provided in order that the alkali metal sulphite or ammonium sulphite may act as both the reducing agent and as the acid acceptor.

The proportion of alkali metal sulphite or ammonium sulphite used as the reducing agent should be at least the stoichiometrically required amount and is preferably at least about 1.2 times, more preferably at least about 1.5 times, the stoichiometrically required amount. The stoichiometrically required amount is 1 mole for each mole of halocarbon to be reduced.

The proportion of the alkali metal sulphite or ammonium sulphite used as the acid acceptor may also be at least the stoichiometrically required amount, that is 1 mole for each mole of acid to be accepted which corresponds to each mole of halocarbon reduced, and preferably is about the stoichiometrically required amount, since if substantially more than the stoichiometrically required amount is employed, the amount of alkene produced may be increased. The amount of alkali metal sulphite or ammonium sulphite employed as the acid acceptor is therefore preferably between about 90% and about 110% of the amount stoichiometrically required, that is between about 0.9 and about 1.1 moles of alkali metal sulphite or ammonium sulphite for each mole of halocarbon to be reduced.

In the preferred embodiment where the same alkali metal sulphite or ammonium sulphite is used as both the reducing agent and the acid acceptor, the stoichiometrically required amount of alkali metal sulphite or ammonium sulphite is 2 moles for each mole of halocarbon to be reduced. Preferably the amount of alkali metal sulphite or ammonium sulphite employed is at least about 1.9 moles of alkali metal sulphite or ammonium sulphite, more preferably at least about 2.2 moles of alkali metal sulphite or ammonium sulphite for each mole of halocarbon to be reduced.

The group —$CX_2Y$ of the halocarbon starting material may comprise three atoms of the same halogen, for example —$CCL_3$ and —$CBr_3$, or it may contain more than one halogen, for example the group may be —$CCl_2Br$ or —$CBr_2Cl$. Furthermore, the group may also contain up to one fluorine atom, for example the group may be —$CCl_2F$ or —$CClBrF$. Typically however the group will contain chlorine optionally with up to one fluorine atom also being present, that is the group will be —CCl$_2$Y where Y is Cl or F. The invention will be described hereafter with reference to halocarbons containing —CCl$_2$Y groups wherein Y is Cl or F although it is to be understood that the invention is not limited to such halocarbons.

The halocarbon containing the group —CX$_2$Y may have the formula R—CX$_2$Y wherein R is as hereinafter described. The group may be a halogen atom, for example Cl, or it may be an aliphatic group and may contain one carbon atom, two carbon atoms, three carbon atoms or even more, say up to 6 carbon atoms. The aliphatic group K may be saturated or unsaturated, cyclic or acyclic, and may, and typically will, be halogenated. The group R may be perhalogenated or it may comprise hydrogen. Typically, the group R will be an optionally halogenated alkyl group, and the halocarbon may be for example, CCl$_3$F, CCl$_3$CF$_3$, CCl$_2$FCF$_3$, CCl$_3$CF$_2$H or CCl$_3$CF$_2$CF$_3$. The structure of the portions of the halocarbon besides the —CX$_2$Y is not critical, and halocarbons with any structures but which contain the —CX$_2$Y group may be reduced in the process of the invention.

The process of the invention is useful for the production of 1,1-dichloro-2,2,3,3,3-pentafluoropropane and according to a particular embodiment of the invention there is provided a process for the production of 1,1-dichloro-2,2,3,3,3-pentafluoropropane which comprises subjecting 1,1,1-trichloro-2,2,3,3,3-pentafluoropropane to a reduction reaction in an aqueous solution of an alkali metal sulphite or ammonium sulphite and an acid acceptor which is an alkali metal sulphite or ammonium sulphite.

The quantity of water required for dissolving the alkali metal sulphite and/or ammonium sulphite may be varied within wide limits, depending at least to some extent upon the particular sulphite employed and the conditions of temperature and pressure, but sufficient water may be used so that the entire quantities of alkali metal sulphite and/or ammonium sulphite are dissolved at the reaction temperature and pressure employed. It is generally unnecessary to use a large excess of water. Overall, at least two moles of water are usually employed for each mole of sulphite employed and where the sulphite employed is the preferred sodium sulphite, we prefer to employ at least 5 moles of water per mole of sodium sulphite.

The temperature at which the reaction is carried out is typically within the range from about 60° C. to about 150° C. and preferably is within the range from about 90° C. to about 110° C. The reaction may be carried out at superatmospheric or subatmospheric pressures; the reaction is conveniently carried out at autogenous pressures in a sealed vessel.

The process according to the invention is suitably carried out in an autoclave. The autoclave may be charged with predetermined quantities of water, halocarbon, reducing agent and acid acceptor and these may then be mixed together. The reaction may be accomplished by maintaining the mixture in the autoclave at a predetermined temperature, preferably with stirring. Pressure increases during the reaction and the heating may be terminated when the pressure in the autoclave is no longer rising, showing that the reaction has been completed. After cooling the product mixture, the organic layer containing the desired product may be separated from the aqueous layer and the organic layer may be purified by conventional means.

Although the amount of alkene by-products may be substantially reduced, there may still be a small amount in the desired product which it is desirable to remove. This may be achieved, for example, by mixing the organic layer with a manganese (VII) salt, for example potassium permanganate and sodium hydroxide in order to oxidise the alkene.

The resulting manganese ((IV) salt may then be reduced to water soluble manganese (II) which may then be separated from the purified organic layer. The reduction of manganese (IV) to manganese (II) may conveniently be achieved, for example, by adding the aqueous layer produced in the reduction process and containing bisulphite to the manganese (IV) solution and acidifying the mixture to pH 1 to 2 with a strong acid, for example sulphuric acid. The organic layer may then be washed, dried and distilled to produce the desired product.

The invention is illustrated but not limited by the following examples.

EXAMPLE 1

(a) Reduction of 1,1,1-trichloro-2,2,3,3,3-pentafluoropropane.

57.1 g, 0.46 moles of anhydrous sodium sulphite was dissolved in 310 ml of distilled water in a 500 ml Hastelloy "C" autoclave and 55.9 g of impure 1,1,1-trichloro-2,2,3,3,3-pentafluoropropane was added. The composition of the impure 1,1,1-trichloro-2,2,3,3,3-pentafluoropropane was:

1,1,1-trichloro- 90.5% 2,2,3,3,3-pentafluoropropane (0.21 moles)

1,1,3-trichloro- 5.3% 1,2,2,3,3-pentafluoropropane tetrachloromethane 4.2%

The autoclave was sealed and the contents of the autoclave were stirred and heated in a furnace to 92° C. during which the pressure rose to 33 psig. After 22 hours, the pressure was no longer rising and was 45 psig. The autoclave was cooled and the liquid contents decanted. Two clear, colourless liquid layers were obtained. The lower organic layer weighed 45.7 g and was separated and analysed by gas chromatography. The results of the analysis are shown in Table 1.

TABLE 1

| ORGANIC PRODUCT | % YIELD BASED ON ORGANIC PRODUCT |
|---|---|
| 1,1-dichlorotetrafluoroprop-1-ene | 2.1% |
| 1,1,-dichloro-2,2,3,3,3-pentafluoropropane | 55.3% |
| 1,3,-dichloro-1,2,2,3,3-pentafluoropropane | 0.7% |
| 1,1,3-trichloro-1,2,2,3,3-pentafluoropropane | 4.6% |
| 1,1,1-trichloro-2,2,3,3,3-pentafluoropropane | 33.5% |
| Chloroform | 3.8% |

The results show a selectivity to 1,1,-dichloro-2,2,3,3,3-pentafluoropropane of 96.3% and to 1,1-dichlorotetrafluoroprop-1-ene of 3.7% with a conversion of 1,1,1-trichloro-2,2,3,3,3-pentafluoropropane of 63%.

(b) Alkaline Permanganate Oxidation of 1,1-dichlorotetrafluoroprop-1-ene.

2.98 g of potassium permanganate and 1.5 g of sodium hydroxide were dissolved in 50 ml of de-ionised water. A mixture of 10.03 g of the product from example 1(a) and 0.1107 g of cyclopentane (added as an internal standard for the Gas chromatography analysis) was added and the mixture was vigorously stirred at room temperature. Samples were withdrawn periodically, and the ratio of 1,1-dichlorotetrafluoroprop-1-ene to cyclopentane by area on a gas chromatagram trace was determined. The results are shown in Table 2 below.

TABLE 2

| TIME/minutes. | RATIO ALKENE AREA/STANDARD AREA |
|---|---|
| 0 | 0.75 |
| 15 | 0.56 |
| 45 | 0.47 |
| 92 | 0.29 |
| 172 | 0.14 |
| 263 | 0.07 |
| 360 | 0.03 |
| 720 | 0.006 |

The mixture was then acidified to pH 1 by adding cold 65% sulphuric acid and excess sodium metabisulphite solution. A near colourless aqueous layer was formed. The organic layer was separated and 8.1 g was obtained. Gas chromatography showed that the amount of 1,1,-dichloro-2,2,3,3,3-pentafluoropropane remained unchanged throughout this purification treatment.

COMPARATIVE EXAMPLE 1

37.8 g, 0.3 moles of anhydrous sodium sulphite and 27.2 g, 0.2 moles of sodium acetate trihydrate were placed in a 500 ml Hastelloy "C" autoclave.

150 ml of distilled water and 47.6 g of impure 1,1,1-trichloro-2,2,3,3,3-pentafluoropropane were added.

The composition of the impure 1,1,1-trichloro-2,2,3,3,3-pentafluoropropane was:

| | |
|---|---|
| Dichlorodecafluoropentane | 0.9% |
| 1,1,1-trichloro-2,2,3,3,3-pentafluoropropane | 92.1% |
| 1,1,3-trichloro-1,2,2,3,3-pentafluoropropane | 5.4% |
| tetrachloromethane | 1.6% |

The autoclave was sealed, leak tested to 200 psig with high purity nitrogen, and then purged to atmospheric pressure twice with 200 psig high purity nitrogen. The contents of the autoclave were stirred and the autoclave was heated in a furnace to an internal temperature of 114° C.; the pressure was 55 psig. After 16 hours the pressure remained constant at 86 psig. The autoclave was cooled and the contents decanted from the autoclave. Two clear, colourless liquid layers were obtained. On standing the aqueous layer deposited some crystals which were dissolved by the addition of water. The lower organic layer was separated and washed with 5% sodium carbonate solution and water, and then dried. 34.3 g of a clear, colourless liquid was obtained. The material was analysed by gas chromatography and the results are shown in Table 3.

TABLE 3

| ORGANIC PRODUCT | % YIELD BASED ON ORGANIC PRODUCT |
|---|---|
| 1,1-dichlorotetrafluoroprop-1-ene | 5.2% |
| 1,1-dichloro-2,2,3,3,3-pentafluoropropane | 69.7% |
| 1,3-dichloro-1,2,2,3,3-pentafluoropropane | 0.4% |

TABLE 3-continued

| ORGANIC PRODUCT | % YIELD BASED ON ORGANIC PRODUCT |
|---|---|
| 1,1,3-trichloro-1,2,2,3,3-pentafluoropropane | 5.0% |
| 1,1,1-trichloro-2,2,3,3,3-pentafluoropropane | 18.2% |
| Chloroform | 1.5% |

The results show a selectivity to 1,1,-dichloro-2,2,3,3,3-pentafluoropropane of 93.0% and to 1,1-dichlorotetrafluoroprop-1-ene of 7.0% with a conversion of 1,1,1-trichloro-2,2,3,3,3-pentafluoropropane of 80%.

We claim:

1. A process for the reduction of a halocarbon containing a group having the formula $-CX_2Y$ wherein X is Cl, Br, or I and Y is Cl, Br, I or F wherein one Cl, Br or I atom of the halocarbon to be reduced is substituted by a hydrogen atom which process comprises subjecting the halocarbon to a reduction reaction in an aqueous solution of (i) at least one mole of an alkali metal sulphite or ammonium sulphite as reducing agent per mole of halocarbon to be reduced and (ii) an acid acceptor, characterised in that as acid acceptor there is employed at least 0.9 mole of an alkali metal sulphite or ammonium sulphite per mole of halocarbon to be reduced in addition to the alkali metal sulfite or ammonium sulfite employed as the reducing agent provided that the total amount of the one or more alkali metal sulphites or ammonium sulphite employed in the process is greater than 2 moles per mole of halocarbon to be reduced.

2. A process as claimed in claim 1 in which the reducing agent is sodium sulphite.

3. A process as claimed in claim 1 in which the acid acceptor is sodium sulphite.

4. A process as claimed in claim 1 in which the same alkali metal sulphite or ammonium sulphite is employed as the reducing agent and acid acceptor.

5. A process as claimed in claim 4 in which the alkali metal sulphite is sodium sulphite.

6. A process as claimed in claim 5 in which at least the stoichiometrically required amount of sodium sulphite is employed.

7. A process as claimed in claim 6 in which at least 2.5 moles of sodium sulphite are employed for each mole of halocarbon to be reduced.

8. A process as claimed in any one of claims 1 to 7 in which the halocarbon contains a group having the formula $-CCl_2Y$ where Y is Cl or F.

9. A process as claimed in claim 8 in which the halocarbon has the formula $R-CCl_2Y$ where Y is Cl or F and R is an optionally substituted alkyl group.

10. A process as claimed in claim 9 wherein the halocarbon is 1,1,1-trichloro-2,2,3,3,3-pentafluoropropane.

11. A process as claimed in any one of claims 1 to 7 in which the temperature is in the range from about 60° C. to about 150° C.

12. A process as claimed in any one of claims 1 to 7 in which an organic product of the process is contacted with potassium permanganate and sodium hydroxide whereby to oxidise any toxic alkene present.

13. A process according to claim 1 wherein the total amount of the one or more alkali metal sulphites or ammonium sulphite employed in the process is greater than 2.2 moles per mole of halocarbon to be reduced.

* * * * *